US009031195B2

(12) United States Patent
Ashokan et al.

(10) Patent No.: US 9,031,195 B2
(45) Date of Patent: May 12, 2015

(54) IMAGING DETECTOR AND METHODS FOR IMAGE DETECTION

(75) Inventors: Renganathan Ashokan, Brookfield, WI (US); Reinaldo Gonzalez, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 639 days.

(21) Appl. No.: 13/112,557

(22) Filed: May 20, 2011

(65) Prior Publication Data

US 2012/0294416 A1 Nov. 22, 2012

(51) Int. Cl.
*A61B 6/00* (2006.01)
*G01T 1/20* (2006.01)
*H01L 27/146* (2006.01)
*A61B 6/03* (2006.01)

(52) U.S. Cl.
CPC ............... *A61B 6/4216* (2013.01); *A61B 6/032* (2013.01); *G01T 1/2002* (2013.01); *G01T 1/2018* (2013.01); *H01L 27/14627* (2013.01); *H01L 27/14663* (2013.01); *A61B 6/508* (2013.01)

(58) Field of Classification Search
CPC ............... G01T 1/2002; G01T 1/2018; H01L 27/14627; A61B 6/032; A61B 6/4216
USPC ..................... 378/98.3; 250/370.11
See application file for complete search history.

(56) References Cited

U.S. PATENT DOCUMENTS

| | | | |
|---|---|---|---|
| 5,463,225 A | 10/1995 | Kwasnick et al. | |
| 5,516,712 A | 5/1996 | Wei et al. | |
| 5,617,463 A * | 4/1997 | Beierlein | 378/98.3 |
| 5,710,801 A * | 1/1998 | Dillen et al. | 378/98.7 |
| 2006/0138335 A1* | 6/2006 | Vogtmeier et al. | 250/370.11 |
| 2007/0194400 A1* | 8/2007 | Yokoyama | 257/443 |
| 2008/0169523 A1* | 7/2008 | Vigier-Blanc et al. | 257/432 |
| 2010/0270462 A1* | 10/2010 | Nelson et al. | 250/252.1 |
| 2011/0026130 A1* | 2/2011 | Winston et al. | 359/641 |

OTHER PUBLICATIONS

Moore, Duncan T., "Gradient Index Optics", Handbook of Optics: Devices, Measurements, and Properties, Second Edition, vol. 2, 1995, Chapter 9, pp. 9.1-9.10.*

* cited by examiner

*Primary Examiner* — Glen Kao
(74) *Attorney, Agent, or Firm* — Dean D. Small; The Small Patent Law Group, LLC

(57) ABSTRACT

An imaging detector includes a scintillator having a scintillator pixel that is configured to emit light. The detector also includes a photosensor that defines a photosensor pixel that is configured to absorb light emitted by the scintillator pixel. A lens is positioned between the scintillator pixel and the photosensor pixel for directing light emitted from the scintillator to the photosensor pixel. The lens is configured to converge light emitted from the scintillator pixel toward the photosensor pixel.

19 Claims, 5 Drawing Sheets

IMAGING DETECTOR AND METHODS FOR IMAGE DETECTION

BACKGROUND OF THE INVENTION

The subject matter disclosed herein relates generally to imaging systems, and more particularly to imaging detectors and methods for image detection.

Imaging systems are widely used to capture images of objects. For example, diagnostic images of a person or an animal may be obtained to assist a doctor or other health care professional in making an accurate diagnosis. Another example includes imaging luggage, shipping containers, and/or the like for security and/or industrial inspection applications. Imaging systems often include an energy source and one or more detectors. Energy, for example x-rays, produced by the source travel through the object being imaged and are detected by the detector(s). An associated control system obtains image data from the detector(s) and prepares a corresponding image for display.

The detectors of at least some known imaging systems include a scintillator, a photosensor array, and an optical coupler that optically couples the scintillator to the photosensor array. The scintillator receives energy emitted by the source that has traveled through the object and emits light in response thereto. The light emitted by the scintillator is directed to the photosensor array by the optical coupler. The photosensor array includes individual photosensors, for example photodiodes, that correspond to individual pixels of the resulting image. The photosensors absorb the light emitted by the scintillator and generate electrical signals that correspond to the absorbed light and are used to create the pixels of the resulting image. However, the photosensors of at least some known photosensor arrays are closely positioned together, which can cause optical and/or electrical cross talk between neighboring photosensors within the array. The optical and/or electrical crosstalk between neighboring photosensors may cause system noise, thereby resulting in a lower quality image.

BRIEF DESCRIPTION OF THE INVENTION

In one embodiment, an imaging detector includes a scintillator having a scintillator pixel that is configured to emit light. The detector also includes a photosensor that defines a photosensor pixel that is configured to absorb light emitted by the scintillator pixel. A lens is positioned between the scintillator pixel and the photosensor pixel for directing light emitted from the scintillator to the photosensor pixel. The lens is configured to converge light emitted from the scintillator pixel toward the photosensor pixel.

In another embodiment, an imaging system is provided for imaging an object. The imaging system includes a source configured to emit energy toward the object, and a detector configured to receive energy emitted from the source that has traveled through the object. The detector includes a scintillator having a scintillator pixel that is configured to emit light, and a photosensor defining a photosensor pixel that is configured to absorb light emitted by the scintillator pixel. A lens is positioned between the scintillator pixel and the photosensor pixel for directing light emitted from the scintillator to the photosensor pixel. The lens is configured to converge light emitted from the scintillator pixel toward the photosensor pixel.

In another embodiment, a method is provided for image detection. The method includes emitting light from a scintillator pixel, converging the light emitted from the scintillator pixel toward a photosensor pixel, and absorbing the converged light at the photosensor pixel.

DETAILED DESCRIPTION OF THE INVENTION

Figure 1:
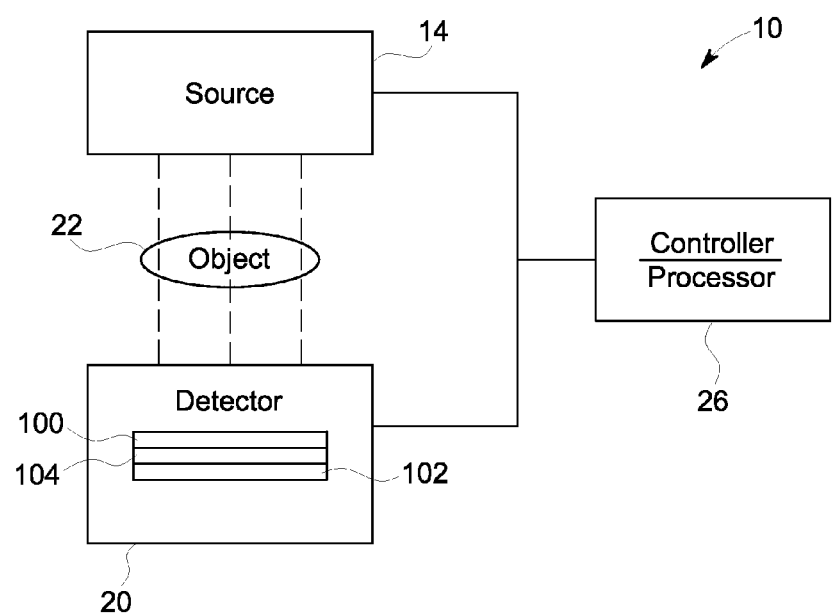
FIG. 1 is a simplified schematic block diagram of an exemplary embodiment of an imaging system.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the term "reconstructing" or "rendering" an image or data set is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image. In an exemplary embodiment, the "object" being imaged is a human individual. However, the object may alternatively be of another living creature besides a human individual. Moreover, the object is not limited to living creatures, but rather may be of inanimate objects, such as, but not limited to, luggage, shipping containers, and/or the like.

Various embodiments provide imaging detectors, imaging systems, and methods for image detection. For example, various embodiments of imaging detectors, imaging systems, and methods for image detection converge light emitted from a scintillator pixel toward the photosensor pixel. At least one technical effect of the various embodiments is a detector having a reduced amount of optical and/or electrical cross talk between neighboring photosensors. At least one other technical effect of the various embodiments is a reduced amount of system noise. At least one other technical effect of the various embodiments is improved image quality.

The various embodiments may be implemented within imaging systems, which include computed tomography (CT) systems, magnetic resonance (MR) systems, ultrasound systems, positron emission tomography (PET) systems, nuclear medicine systems, and other types of imaging systems. Applications of image systems include medical applications, security applications, industrial inspection applications, and/or the like. An exemplary embodiment is described and illustrated herein with respect to a CT imaging system 300 having detectors 320 that detect x-rays. However, the various embodiments described and/or illustrated herein may be used with any other imaging modality and may be used to detect any other type of electromagnetic energy. Moreover, the various embodiments described and/or illustrated herein are applicable with single slice and/or multi-slice configured systems.

Referring now to FIG. 1, an imaging system 10 includes a source 14 of electromagnetic energy, one or more detectors 20, and a controller/processor 26. The controller/processor 26 may provide power and/or timing signals to the source 14. The detector 20 senses energy emitted by the source 14 that has passed through an object 22 being imaged. In response thereto, the detector 20 produces an electrical signal that represents the sensed energy. The detector 20 includes a scintillator 100, a photosensor array 102, and a converging component (e.g., a lens array) 104 for directing light emitted by the scintillator 100 to the photosensor array 102. The controller/processor 26 samples analog data from the detector 20, converts the data to digital signals for subsequent processing, and performs image reconstruction. The reconstructed image may be stored and/or displayed by the controller/processor 26 and/or another device.

Figure 2:
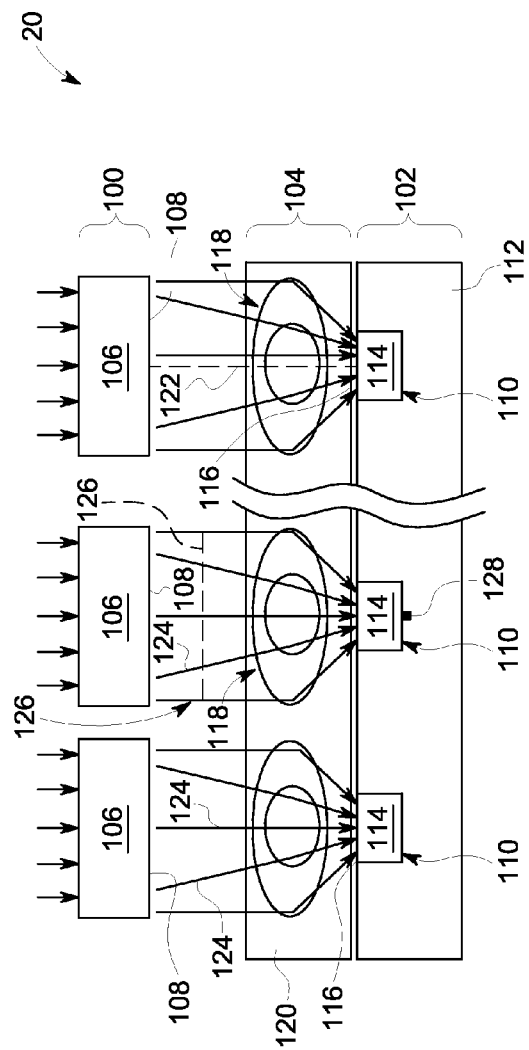
FIG. 2 is an elevational schematic view of an exemplary embodiment of an imaging detector of the imaging system shown in FIG. 1.
Figure 3:
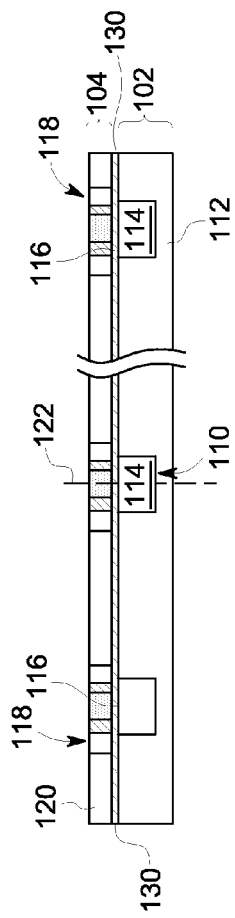
FIG. 3 is a cross-sectional schematic view of a portion of the detector shown in FIG. 2.

FIG. 2 is an elevational schematic view of an exemplary embodiment of the detector 20. FIG. 3 is a cross-sectional schematic view of a portion of the detector 20. The detector 20 includes the scintillator 100, the photosensor array 102, and the lens array 104. The scintillator is not shown in FIG. 3. The scintillator 100 is fabricated from a scintillating medium that is configured to emit optical photons, or light, in response to the absorption of electromagnetic energy (e.g., x-rays) that has traveled through the object being imaged (e.g., the object 22 shown in FIG. 1 or the patient 322 shown in FIGS. 6 and 7). One example of a suitable scintillating medium for use with x-rays is cesium iodide doped with thallium (CsI:Tl). However, other suitable materials may be used. The scintillator 100 comprises a plurality of individual scintillator pixels 106. In response to energy received from a source (e.g., the source 14 shown in FIG. 1 or the x-ray source 314 shown in FIGS. 6 and 7) that has traveled through the object being imaged, each scintillator pixel 106 is configured to emit light that corresponds to a pixel in the resulting image. Each scintillator pixel 106 includes an active area 108 from which light is emitted. The active areas 108 are visible in only a single dimension in FIGS. 2 and 3. However, it should be appreciated that the active areas 108 are each two-dimensional areas, which is better illustrated in FIG. 4. Each active area 108 may be referred to herein as an "active scintillator area".

The photosensor array 102 includes a plurality of individual photosensors 110, which may be arranged in a plurality of rows and/or columns on a substrate 112. The substrate 112 may include only a single layer, or may be a multi-layered structure. Each photosensor 110 is a photosensitive element that is configured to absorb light emitted by a corresponding scintillator pixel 106 and generate an electrical charge in response thereto. One example of a photosensitive element includes amorphous silicon. However, other suitable materials may be used. The DAS 32 (FIG. 2) is operatively connected to each of the photosensors 110 for receiving the electrical signals generated thereby. The photosensors 110 may be any type of photosensor, such as, but not limited to, photodiodes.

Each photosensor 110 defines a photosensor pixel 114 that absorbs light emitted by a corresponding one of the scintillator pixels 106. The electrical signal generated by each photosensor pixel 114 corresponds to a pixel in the resulting image. Each photosensor pixel 114 includes an active area 116 wherein light is absorbed. The active areas 116 are visible in only a single dimension in FIGS. 2 and 3. However, it should be appreciated that the active areas 116 are each two-dimensional areas, which is better illustrated in FIG. 4. Each active area 116 may be referred to herein as an "active photosensor area".

Figure 4:
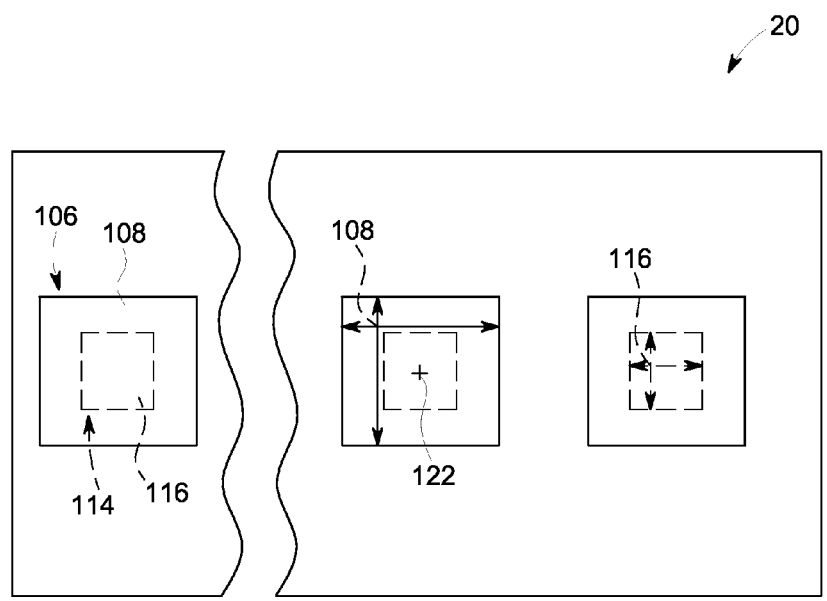
FIG. 4 is a plan schematic view of the detector shown in FIGS. 2 and 3.
Figure 5:
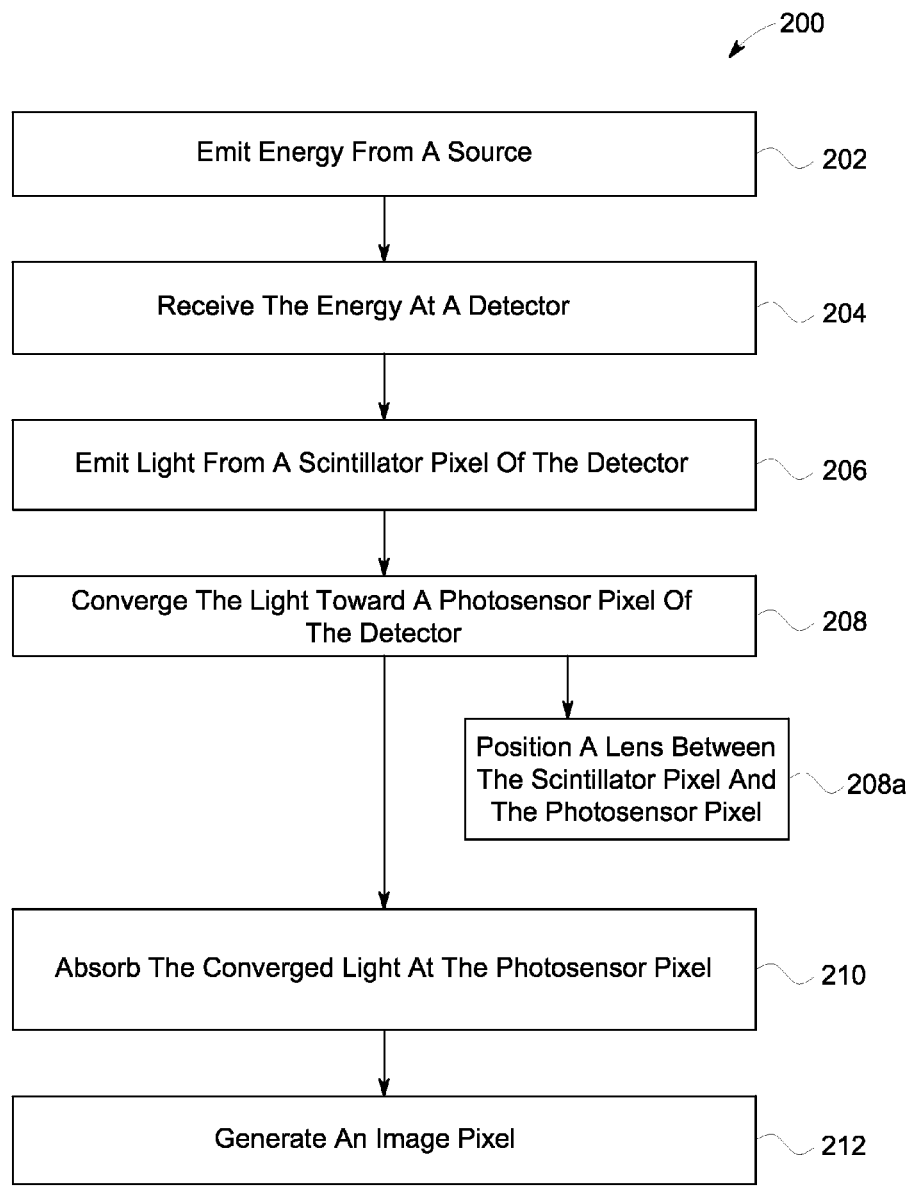
FIG. 5 is a flowchart illustrating an exemplary embodiment of a method for image detection.

FIG. 4 is a plan schematic view of the detector 20 illustrating the relative size between the active areas 108 of the scintillator pixels 106 and the active areas 116 of the photosensor pixels 114. As can be seen in FIG. 5, the active area 108 of each scintillator pixel 106 is larger than the active area 116 of the corresponding photosensor pixel 114. The active areas 108 of the scintillator pixels 106 may be larger than the active areas 116 of the corresponding photosensor pixels 114 by a predetermined or predefined amount. For example, in some embodiments, the active area 108 of a scintillator pixel 106 is at least three times greater than the active area 116 of the corresponding photosensor pixel 114. Although shown as having a square shape, the active area 108 of each scintillator pixel 106 may have any other shape, such as, but not limited to, circular, oval-shaped, a non-square rectangle, and/or the like. Moreover, the active area 116 of each photosensor pixel 114 may have any other shape besides square (such as, but not limited to, circular, oval-shaped, a non-square rectangle, and/or the like), whether or not such shape is the same as the active area 108 of the corresponding scintillator pixel 106.

Referring again to FIGS. 2 and 3, the lens array 104 is positioned between the scintillator 100 and the photosensor array 102 for directing light emitted by the scintillator 100 to the photosensor array 102. The lens array 104 includes a plurality of lenses 118, which are each sometimes referred to as "microlens". The lens 118 may be held together within the array 102 by a suitable support structure 120, for example a substrate, which may be a single layer or may be comprised of multiple layers. Each lens 118 is positioned between a corresponding scintillator pixel 108 and a corresponding photosensor pixel 114 and directs light emitted from the active area 108 of the scintillator pixel 106 along a central transmission axis 122 to the active area 116 of the photosensor pixel 114.

The lenses 118 are configured to converge light emitted from the corresponding scintillator pixel 106 toward the corresponding photosensor pixel 114. By "converge", it is meant that photons, or light rays, 124 emitted from the active area 108 of the scintillator pixel 106 are brought toward (e.g., radially inwardly toward the central transmission axis 122) each other and toward a common focal point 128 by the lens 118 as the lens 118 directs the light rays 124 to the active area 116 of the corresponding photosensor pixel 114. In other words, the lens 118 reduces a cross-sectional size (e.g., a width, a diameter, and/or the like) of a light beam 126 (which as shown includes the light rays 124) emitted by the corresponding scintillator pixel 106 for delivery to the corresponding photosensor pixel 114. The lens 118 thereby focuses the light beam 126 from the size emitted from the scintillator pixel 106 toward the smaller size of the photosensor pixel 114. Notably, the light rays 124 will not completely converge (meet at the focal point 128) because the light rays 124 will first be absorbed by the active area 116 of the photosensor pixel 114.

Each lens 118 may converge the light rays 124 by any amount. In other words, each lens 118 may reduce the cross-sectional size of a light beam 126 emitted by the corresponding scintillator pixel 106 by any amount. The amount of convergence and/or reduction in cross section may correspond to the size of the active area 116 of the corresponding photosensor pixel 114. In some embodiments, a lens 118 reduces the cross-sectional size of a light beam 126 emitted by the corresponding scintillator pixel 106 such that the cross-sectional size of the beam 126 as received by the active area 116 of the corresponding photosensor pixel 114 is at least three times smaller than the size of the beam 126 as emitted by the active area 108 of the corresponding scintillator pixel 106.

The convergence of the light emitted from the scintillator pixel 106 enables the photosensor pixel 114 to be smaller than the scintillator pixel 106 by any amount. For example, as described above, in some embodiments the active area 116 of the photosensor pixel 114 is at least three times smaller than the active area 108 of the corresponding scintillator pixel 106. Reducing the size of the photosensor pixel 114 relative to the scintillator pixel 106 may reduce the capacitance of the photosensor pixel 114, for example according to the equation:

$$C = \varepsilon \frac{A}{d},$$

wherein A is the area of the photosensor pixel 114, d is the dielectric layer (space charge region) thickness, and $\varepsilon$ is the dielectric constant.

The reduction of photosensor pixel size relative to scintillator pixel size may reduce the capacitance of the photosensor pixel. Consequently, imaging system noise may be reduced and image quality may be improved per the equation: Electronic noise $N \propto \sqrt{2kTC}$, whereing k is the Boltzman constant, T is the temperature, and C is the capacitance. The reduction in system noise results in better image quality.

Moreover, reduction of photosensor pixel size relative to scintillator pixel size increases the available silicon real estate so that additional signal processing circuits may be fabricated between the photosensor pixels 114. The advanced additional electronic circuits may provide access to individual photosensor pixels (known as x-y readout capability) and/or other noise filtering kind of functions. The advantages of having such additional signal processing capability within the photosensor array 102 are numerous as would be evident to a person of ordinary skill in the art.

Each lens 118 may be any type of lens that is configured to converge light emitted by the corresponding scintillator pixel 106 as described and/or illustrated herein. In some embodiments, a lens 118 is a radially graded lens, a refractive index lens, or a radially graded refractive index lens. Optionally, opposite surfaces of the lens array 104 may be parallel to each other and approximately flat, for example to minimize optical losses from surfaces of the lenses 118.

Optionally, an optical coupler 130 (not shown in FIG. 2) is positioned between the lens array 102 and the photosensor array 104, an optical coupler (not shown) is positioned between the lens array 102 and the scintillator 100, and/or an optical coupler (not shown) is positioned within the lens array 102 around one or more of the lenses 118. The optical coupler 130 optically couples the light transmitted through the lens 118 to the photosensors 110. Specifically, the optical coupler 130 may provide a high degree of transmission with little or no scattering of optical photons. The optical coupler 130 may be fabricated from any materials that enable the optical coupler 130 to optically couple light transmitted through the lens 118 to the photosensors 110, such as, but not limited to, a transparent dielectric material that is substantially free of cracks, and/or the like.

Figure 6:
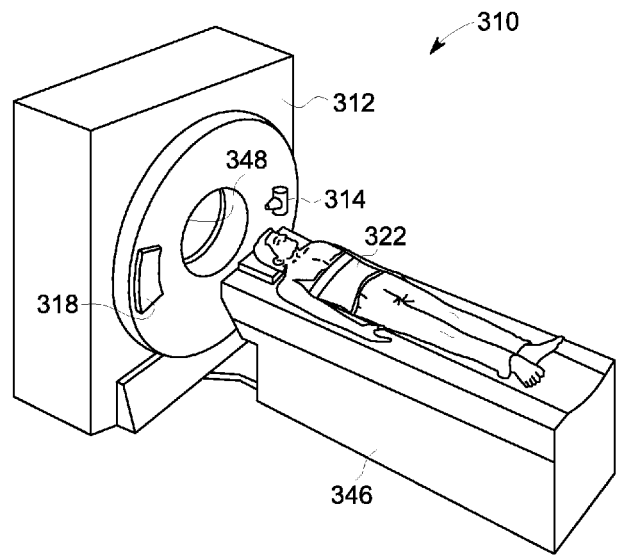
FIG. 6 is a pictorial drawing of a computed tomography (CT) imaging system constructed in accordance with various embodiments.
Figure 7:
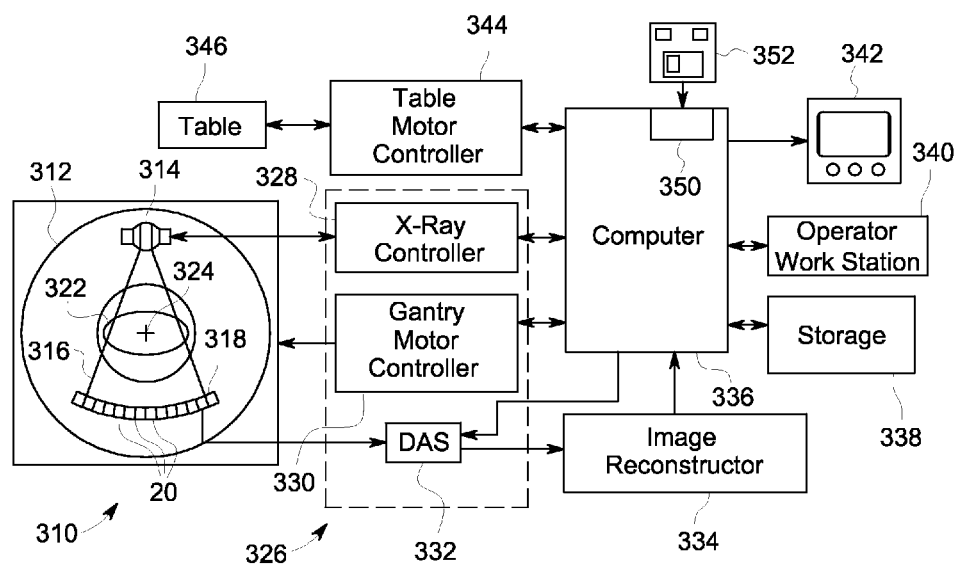
FIG. 7 is a schematic block diagram of the CT imaging system of FIG. 1.

FIG. 5 is a flowchart illustrating an exemplary embodiment of a method 200 for image detection, for example using the imaging system 10 shown and described with respect to FIG. 1, for example the CT imaging system 310 shown and described with respect to FIGS. 6 and 7, and/or for example using the detector 20 shown and described with respect to FIGS. 2-4. At 202, the method 200 includes emitting energy from a source (e.g., the source 14 shown in FIG. 1 or the x-ray source 314 shown in FIGS. 6 and 7). The method 200 includes, at 204, receiving the energy emitted from the source at a detector.

At 206, the method 200 includes emitting light from a scintillator pixel of the detector. The light emitted by the scintillator pixel at 206 is converged at 208 toward a photosensor pixel of the detector. Converging the light at 208 may include positioning a converging component (e.g., a lens) between the scintillator pixel and the photosensor pixel at 208a. In some embodiments, converging the light at 208 includes reducing the cross-sectional area of a beam of light emitted by the scintillator pixel. The method 200 includes absorbing the converged light at the photosensor pixel at 210. The photosensor pixel generates an electrical signal that corresponds to the absorbed light. Optionally, the method 200 includes providing an active area on the photosensor pixel as smaller than an active area of the scintillator pixel.

At 212, the method may include generating an image pixel based on the electrical signal generated by the photosensor pixel from the converged light absorbed thereby. The image pixel may be displayed along with other image pixels within a complete image. In addition or alternative to the method 200, a method may be provided for manufacturing a detector in accordance with the various embodiments described and/or illustrated herein.

Referring to FIGS. 6 and 7, a multi-slice scanning imaging system, for example, a CT imaging system 310 is shown as including a plurality of the detectors 20. The CT imaging system 310 includes a gantry 312, which includes an x-ray tube 314 (also referred to as an x-ray source 314 herein) that projects a beam of x-rays 316 toward a detector array 318 on the opposite side of the gantry 312. The detector array 318 is formed by a plurality of detector rows (not shown) including a plurality of the detectors 20 that together sense the projected x-rays that pass through an object, such as a medical patient 322 between the array 318 and the source 314. Each detector 20 produces an electrical signal that represents the intensity of an impinging x-ray beam and hence can be used to estimate the attenuation of the beam as the beam passes through the patient 322. During a scan to acquire x-ray projection data, the gantry 312 and the components mounted therein rotate about a center of rotation 324. FIG. 7 shows only a single row of detectors 20 (i.e., a detector row). However, the multi-slice detector array 318 includes a plurality of parallel detector rows of detectors 20 such that projection data corresponding to a plurality of quasi-parallel or parallel slices can be acquired simultaneously during a scan.

Rotation of components on the gantry 312 and the operation of the x-ray source 314 are controlled by a control mechanism 326 of the CT imaging system 310. The control mechanism 326 includes an x-ray controller 328 that provides power and timing signals to the x-ray source 314 and a gantry motor controller 330 that controls the rotational speed and position of components on the gantry 312. A data acquisition system (DAS) 332 in the control mechanism 326 samples analog data from the detectors 20 and converts the data to digital signals for subsequent processing. An image reconstructor 334 receives sampled and digitized x-ray data from the DAS 332 and performs high-speed image reconstruction. The reconstructed image is applied as an input to a computer 336 that stores the image in a storage device 338. The image reconstructor 334 can be specialized hardware or computer programs executing on the computer 336. The control mechanism 326, the computer 336, and/or the image reconstructor 334 may be implemented as components of the controller/processor 26 shown in FIG. 1, for example.

The computer 336 also receives commands and scanning parameters from an operator via a console 340 that has a keyboard and/or other user input and/or marking devices, such as a mouse, trackball, or light pen. An associated display 342, examples of which include a cathode ray tube (CRT) display, liquid crystal display (LCD), or plasma display, allows the operator to observe the reconstructed image and other data from the computer 336. The display 342 may include a user pointing device, such as a pressure-sensitive input screen. The operator supplied commands and parameters are used by the computer 36 to provide control signals and information to the DAS 332, x-ray controller 328, and gantry motor controller 330. In addition, the computer 336 operates a table motor controller 344 that controls a motorized table 346 to position the patient 322 in the gantry 312. For example, the table 346 moves portions of the patient 322 through a gantry opening 348.

In one embodiment, the computer 336 includes a device 350, for example, a floppy disk drive, CD-ROM drive, DVD drive, magnetic optical disk (MOD) device, or any other device including a network connecting device such as an Ethernet device for reading instructions and/or data from a computer-readable medium 352, such as a floppy disk, a CD-ROM, a DVD or another source such as a network or the Internet, as well as yet to be developed digital means. In another embodiment, the computer 336 executes instructions stored in firmware (not shown).

As used herein, the term computer is not limited to integrated circuits referred to in the art as computers, but broadly refers to computers, processors, microcontrollers, microcomputers, programmable logic controllers, application specific integrated circuits, and other programmable circuits, and these terms are used interchangeably herein. Further, the CT imaging system may be, for example, different types of CT imaging systems, such as a third generation CT imaging system, a fourth generation CT imaging system (stationary detector-rotating x-ray source) and a fifth generation CT imaging system (stationary detector and x-ray source), as well as first and second generation CT imaging systems. Additionally, as described above, it is contemplated that the benefits of the various embodiments accrue to imaging modalities other than CT and energies other than x-rays. Further, as also described above, although the herein described methods and apparatus are described in a medical setting, it is contemplated that the benefits of the various embodiments accrue to non-human imaging systems such as, but not limited to, those systems typically employed in an animal imaging, in security applications, and/or in industrial inspection applications.

Thus, various embodiments provide imaging detectors, imaging systems, and methods for image detection. The various embodiments may provide improved image quality as compared to at least some known imaging systems. The various embodiments may provide a reduced amount of system noise as compared to at least some known imaging systems. The various embodiments may provide a detector having improved low signal detectability and/or improved low contrast imaging capability as compared to at least some known detectors. The various embodiments may provide a reduced amount of dose required for a patient. The various embodiments may provide a detector having a reduced amount of optical and/or electrical cross talk between neighboring photosensors for a given sized photosensor array than at least some known detectors. The various embodiments may provide a detector having a reduced amount of capacitance and/or a reduced leakage (saturation) current as compared to at least some known detectors. The various embodiments may provide a detector having a reduced or eliminated amount of defects (e.g., gain variations caused by pixel-to-pixel variations) as compared to at least some known detectors. The various embodiments may provide a photosensor array having an increased amount of space for other components (e.g., processing components and/or the like) as compared to at least some known photosensor arrays.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An imaging detector comprising:
a scintillator comprising a scintillator pixel that is configured to emit light;
a photosensor defining a photosensor pixel that is configured to absorb light emitted by the scintillator pixel; and
a lens comprising a radially graded refractive index lens, wherein the lens is held within a lens substrate, the lens positioned between the scintillator pixel and the photosensor pixel for directing light emitted from the scintillator to the photosensor pixel, wherein the lens is configured to converge light emitted from the scintillator pixel toward the photosensor pixel at a focal point, the photosensor is interposed between the lens and the focal point.

2. The imaging detector of claim 1, wherein the scintillator pixel comprises an active scintillator area wherein light is emitted from, the photosensor pixel comprising an active photosensor area wherein light is absorbed, the active photosensor area being smaller than the active scintillator area.

3. The imaging detector of claim 1, wherein the scintillator pixel comprises an active scintillator area wherein light is emitted from, the photosensor pixel comprising an active photosensor area wherein light is absorbed, the active photosensor area being at least three times smaller than the active scintillator area.

4. The imaging detector of claim 1, wherein the photosensor comprises a photodiode.

5. The imaging detector of claim 1, further comprising an optical coupler interposed between the lens and the photosensor that optically couples the light transmitted through the lens to the photosensor.

6. The imaging detector of claim 1, wherein the photosensor is held within a photosensor substrate positioned below the lens substrate.

7. The imaging detector of claim 6, wherein an optical coupler is positioned between the lens substrate and the photosensor substrate such that the optical coupler optically couples the converged light of the lens to the photosensor.

8. The image detector of claim 1, wherein the light emitted from the scintillator pixel is converged by the lens at the focal point such that at least a portion of the light is absorbed by the photosensor before converging at the focal point.

9. An imaging system for imaging an object, the imaging system comprising:
a source configured to emit energy toward the object; and
a detector configured to receive energy emitted from the source that has traveled through the object, the detector comprising:
a scintillator comprising a scintillator pixel that is configured to emit light;
a photosensor defining a photosensor pixel that is configured to absorb light emitted by the scintillator pixel;
a lens comprising a radially graded refractive index lens, wherein the lens is held within a lens substrate, the lens positioned between the scintillator pixel and the photosensor pixel for directing light emitted from the scintillator to the photosensor pixel, wherein the lens is configured to converge light emitted from the scintillator pixel toward the photosensor pixel at a focal point, the photosensor is interposed between the lens and the focal point; and
an optical coupler interposed between the lens and the photosensor that optically couples the light transmitted through the lens to the photosensor.

10. The imaging system of claim 9, wherein the scintillator pixel comprises an active scintillator area wherein light is emitted from, the photosensor pixel comprising an active photosensor area wherein light is absorbed, the active photosensor area being smaller than the active scintillator area.

11. The imaging system of claim 9, wherein the scintillator pixel comprises an active scintillator area wherein light is emitted from, the photosensor pixel comprising an active photosensor area wherein light is absorbed, the active photosensor area being at least three times smaller than the active scintillator area.

12. The imaging system of claim 9, wherein the photosensor comprises a photodiode.

13. The imaging system of claim 9, wherein the optical coupler is fabricated from transparent dielectric material.

14. The imaging system of clam 9, wherein the source is configured to emit x-rays and the imaging system is a computed tomography (CT) system.

15. The imaging detector of claim 9, wherein the photosensor is held within a photosensor substrate positioned below the lens substrate.

16. A method for image detection, the method comprising:
emitting light from a scintillator pixel;
converging the light emitted from the scintillator pixel toward a photosensor pixel by positioning a lens comprising a radially graded refractive index lens within a lens substrate between the scintillator pixel and the photosensor pixel, wherein the lens is configured to converge light emitted from the scintillator pixel toward the photosensor pixel at a focal point; and
absorbing the converged light at the photosensor pixel, wherein the photosensor is interposed between the lens and the focal point 17. The method of claim 16, wherein the light emitted from the scintillator pixel is a beam of light, and wherein converging the light comprises reducing a cross-sectional area of the beam of light.

18. The method of claim 16, wherein the scintillator pixel comprises an active scintillator area wherein light is emitted from, and the photosensor pixel comprises an active photosensor area wherein light is absorbed, the method further comprising providing the active photosensor area as smaller than the active scintillator area.

19. The method of claim 16, further comprising generating an image pixel based on the converged light absorbed by the photosensor pixel.

* * * * *